United States Patent [19]

Pastor et al.

[11] Patent Number: 5,334,739
[45] Date of Patent: Aug. 2, 1994

[54] PROCESS AN ALPHA MONOCLINIC CRYSTALLINE MODIFICATION OF 2,2',2''-NITRILO[TRIETHYL-TRIS-(3,3',5,5'-TETRA-TERT-BUTYL-1,1'-BIPHENYL-2,2'-DIYL)PHOSPHITE]

[75] Inventors: Stephen D. Pastor, Danbury, Conn.; Sai P. Shum, Hawthorne, N.Y.; Paul A. Odorisio, Edgewater, N.J.

[73] Assignee: Ciba-Geigy Corporation, Ardsley, N.Y.

[21] Appl. No.: 983,180

[22] Filed: Nov. 30, 1992

[51] Int. Cl.$^5$ ............................................. C07F 9/6574
[52] U.S. Cl. ................................... 558/78; 524/119
[58] Field of Search ........................ 558/78; 524/119

[56] References Cited

U.S. PATENT DOCUMENTS 4,318,845  3/1982  Spivack et al. ..................... 524/91
4,374,219  2/1983  Spivack et al. ..................... 524/91

OTHER PUBLICATIONS

L. C. Cross, et al. Pure Appl. Chem 45, 11–30 (1976).
G. Gold, et al., J. Pharm. Sci., 55, 1291 (1966).

*Primary Examiner*—Mary C. Lee
*Assistant Examiner*—Michael G. Ambrose
*Attorney, Agent, or Firm*—Luther A. R. Hall

[57] ABSTRACT

The alpha crystalline modification of 2,2',2''-nitrilo[triethyl-tris-(3,3',5,5'-tetra-tert-butyl-1,1'-biphenyl-2,2'-diyl) O'Z phosphite] is obtained by crystallizing said compound from selected solvents, preferably from a mixture of an aromatic hydrocarbon solvent and a lower alkanol.

The alpha crystalline form is an effective process stabilizer for polyolefins, particularly polypropylene.

5 Claims, No Drawings

PROCESS AN ALPHA MONOCLINIC CRYSTALLINE MODIFICATION OF 2,2',2''-NITRILO[TRIETHYL-TRIS-(3,3',5,5'-TETRA-TERT-BUTYL-1,1'-BIPHENYL-2,2'-DIYL)PHOSPHITE]

This invention pertains to a novel crystalline modification of 2,2',2''-nitrilo[triethyl-tris-(3,3',5,5'-tetra-tert-butyl-1,1'-biphenyl-2,2'-diyl) phosphite] and to a process for preparing said modification.

BACKGROUND OF THE INVENTION 2,2',2''-Nitrilo[triethyl-tris-(3,3',5,5'-tetra-tert-butyl-1,1'-biphenyl-2,2'-diyl) phosphite] is a compound having the formula I

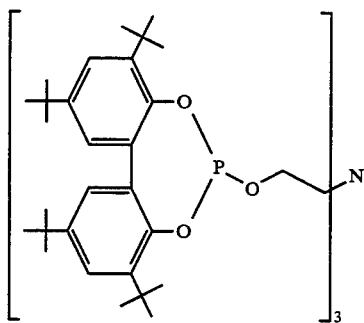

(I)

This compound of formula I is useful as a processing stabilizer for organic polymers as taught in U.S. Pat. Nos. 4,318,845 and 4,374,219. The compound of formula I is disclosed as being a white powder melting at 121°–134° C. As such, the powdery product has defects in terms of handling and apparent density, exhibiting poor flowability, meterability, storage stability and hydrolytic stability.

It has now been found that the compound of formula I can be obtained in a different crystalline modification as purified crystalline particles which exhibit acceptable properties in respect to handling, apparent density, flowability, meterability, storage stability and hydrolytic stability.

The new modification is characterized by a monoclinic crystalline form, melting in the range of 145°–165° C. as given by the peak temperature of the endotherm recorded by differential scanning calorimetry (DSC); and by an X-ray diffraction pattern obtained using Cu-Kα which exhibits diffraction angles (2Θ) of relative intensity given in the table below.

| Diffraction Angle (2Θ) | Relative Intensity (%) |
| --- | --- |
| 5.2 | 100 |
| 5.8 | 38 |
| 6.3 | 13 |
| 6.5 | 15 |
| 7.2 | 14 |
| 8.0 | 30 |
| 8.7 | 31 |
| 8.9 | 36 |
| 10.0 | 35 |
| 10.1 | 31 |
| 10.7 | 41 |
| 11.6 | 18 |
| 12.7 | 7 |
| 13.6 | 20 |
| 14.2 | 23 |
| 14.9 | 18 |
| 15.7 | 30 |
| 16.2 | 31 |
| 16.6 | 48 |
| 17.0 | 28 |
| 17.4 | 58 |
| 18.2 | 37 |
| 18.7 | 20 |
| 19.6 | 20 |
| 20.0 | 17 |
| 20.2 | 17 |
| 20.8 | 17 |
| 21.1 | 18 |
| 22.6 | 18 |
| 22.7 | 18 |
| 22.9 | 18 |
| 23.1 | 16 |

The X-ray diffraction pattern thus shows angles (2Θ) lines of very high intensity at 5.2; lines of high intensity at 10.7, 16.6 and 17.4; lines of medium intensity at 5.8, 8.0, 8.9, 10.0, 10.1, 10.7, 15.7, 16.2 and 18.2; lines of weak intensity at 6.3, 6.5, 7.2, 11.6, 12.7, 13.6, 14.2, 14.9, 17.0, 18.7 and 19.6; and a relative absolute configuration of the three stereo axes of the dibenzo[d,f][1,3,2]dioxaphosphepin rings of R*,R*,R*.

R* follows the customary convention when the absolute configuration of a molecule is unknown. The nomenclature adopted here is based on recent Chemical Abstracts Service practice as described by L. C. Cross and W. Kylne, Pure Appl. Chem. 45, 11–30 (1976).

The instant invention also relates to processes for the preparation of this novel alpha crystalline modification of the compound of formula I.

The instant invention also pertains to a composition stabilized against thermal, oxidative and actinic induced degradation which comprises (a) a polyolefin, and (b) an effective mount of the alpha crystalline form of 2,2',2''-nitrilo[triethyl-tris-(3,3',5,5'-tetra-tert-butyl-1,1'-biphenyl-2,2'-diyl) phosphite], characterized by melting in the range of 145°–165° C. and by an X-ray diffraction pattern exhibiting lines of very high intensity at 5.2; lines of high intensity at 10.7, 16.6 and 17.4; lines of medium intensity at 5.8, 8.0, 8.9, 10.0, 10.1, 10.7, 15.7, 16.2 and 18.2; lines of weak intensity at 6.3, 6.5, 7.2, 11.6, 12.7, 13.6, 14.2, 14.9, 17.0, 18.7 and 19.6; and a relative configuration of the three dibenzo[d,f][1.3.2]dioxaphosphepin rings of R*,R*,R*.

Preferably, the polyolefin is polypropylene.

The instant alpha crystalline modification is obtained by a process of crystallizing or recrystallizing the compound of formula I from a mixture of an aromatic hydrocarbon solvent and an alcohol of 1 to 3 carbon atoms; from an ether solvent; from an ester solvent; or from a mixture of a halogenated aliphatic hydrocarbon solvent and a lower carbon chain alcohol.

The preferred process for preparing the novel alpha crystalline modification is by crystallizing or recrystallizing the compound of formula I from a mixture of an aromatic hydrocarbon solvent and a lower carbon chain alcohol.

A preferred embodiment of the instant process involves isolating the crystalline mass from any of the above processes and drying it under vacuum at elevated temperature.

Examples of aromatic hydrocarbon solvents useful in the instant process are benzene, toluene, o-xylene, m-xylene, p-xylene, 1,2,3-trimethylbenzene, 1,3,5-trimethylbenzene, 1,2,4-trimethylbenzene, 1,2,4,5-tetramethylbenzene, ethylbenzene, cumene, o-cymene, m-cymene, p-cymene, o-diisopropylbenzene, m-diisopropylbenzene, p-diisopropylbenzene, and mixtures of such aromatic hydrocarbon solvents.

Examples of lower carbon chain alcohols of 1 to 3 carbon atoms are methanol, ethanol, 1-propanol, isopropanol and mixtures of such lower alkanols.

Examples of ester solvents are methyl formate, ethyl formate, methyl acetate, ethyl acetate, n-butyl acetate, isobutyl acetate, amyl acetate and the like.

Examples of ether solvents are diethyl ether, diisopropyl ether, methyl tert-butyl ether and the like.

Examples of halogenated aliphatic hydrocarbon solvents are methylene chloride, chloroform, 1,2-dichloroethane, 1,1,2,2-tetrachloroethane and the like.

Differential scanning calorimetry (DSC) measurements are obtained on a TA Instrument Inc., 910 differential scanning calorimeter, with a 100 mL/min nitrogen purge, aligned aluminum pan, temperature scan at 5° C./min to 230° C.

X-ray diffraction patterns are recorded on a Philips Norelco X-ray Diffractometer unit, using Cu-K$\alpha$ radiation with a nickel filter.

EXAMPLE 1

The compound of formula I, 2,2′,2″-nitrilo[triethyl-tris-(3,3′,5,5′-tetra-tert-butyl-1,1′-biphenyl-2,2′-phosphite], is prepared according to procedure of Example 4 of U.S. Pat. No. 4,318,845. The product obtained is recrystallized from the following solvent systems to obtain the novel alpha crystalline modification of the instant invention.

| Solvent (wt/wt) | Compound/Solvent Ratio (wt/wt) | mp (°C.)* | (%) Yield |
|---|---|---|---|
| ethyl acetate | 1/3.8 | 160 | 74 |
| toluene/isopropanol (1/6) | 1/7 | 158 | 75 |
| xylene/isopropanol (1/1) | 1.2/1 | 159 | 91 |
| xylene/methanol (1.8/1) | 1.5/1 | 159 | 97 |
| toluene/methanol (1/1) | 1/2 | 159 | 91 |
| toluene/methanol (1.1/1) | 1/8.3 | 159 | 50 |
| diethyl ether | 1/3.5 | 165 | 25 |
| isopropanol/dichloromethane (1.2/1) | 1/7.25 | 161 | 38 |
| xylene/1-propanol (1/1) | 1.2/1 | 163 | 93 |

*Melting point is determined by differential scanning calorimetry and the peak temperature in the endotherm is recorded as the melting point.

Suitable crystals for X-ray analysis are grown from ethyl acetate. For the structure determination, a thick hexagonal plate is selected and broken to reduce the largest dimension to less than 1 mm. Intensity data are measured on a Siemens R3MV four circle diffractometer as described in Table 1below. The structure is solved by direct methods using Siemens SHELXTL PLUS (VMS). Full-matrix least-square refinements are carried out. The relative absolute configuration is determined to be R*, R*, R*.

TABLE 1

| Crystal and Data Collection Parameters ||
|---|---|
| Formula | $C_{90}H_{132}NO_9P_3$ |
| Formula weight (g · mol$^{-1}$) | 1464.96 |
| Color; Habit | Colorless Hexagonal Prism |
| Crystal System | Monoclinic |
| Space group | $P2_1/n$ |
| Z | 4 |
| Cell parameters | a = 20.0700 (10) Å |
|  | b = 17.477 (2) Å |
|  | c = 27.620 (3) Å |
|  | $\beta$ = 93.050 (10) deg |
| Volume | $v$ = 9674.5 (14) Å$^3$ |
| $d_{calc}$ | 1.006 |
| Absorption Coefficient | 0.926 mm$^{-1}$ |
| Crystal Size | 0.3 × 0.3 × 0.6 mm |
| F(000) | 3184 |
| Temperature | 23 C. |
| Diffractometer Type | Siemens R3m/V |
| Radiation | CuK$\alpha$ ($\lambda$ = 1.54178 Å) |
| Monochromator | Orientated graphite crystal |
| 2$\theta$ Range | 3.15 to 115.0 deg |
| Scan Type | 2$\Theta - \Theta$ |
| Scan Range (w) | 0.50° plus K$\alpha$ separation |
| Reflections Collected | 14042 |
| No. of observed reflections | 9094 (F > 3.0 $\sigma$ (F)) |
| R | 0.1159 |
| R$_w$ | 0.1690 |

EXAMPLE 2

Comparative Example

The compound of formula I, prepared according to the procedure of Example 4 of U.S. Pat. No. 4,318,845 and not recrystallized according to the procedure of Example 1 of this application, is heated at 210° C. until a clear melt is obtained. The melt is cooled rapidly to ambient temperature to yield a glassy solid with a Tg (DSC) of 105°–110° C. The X-ray diffraction pattern of this product obtained using Cu-K$\alpha$ is featureless.

Analysis: Calcd for $C_{90}H_{132}NO_9P_3$: C, 73.8; H, 9.1; N, 0.96. Found: C, 73.4; H, 9.3; N, 0.9.

EXAMPLE 3

Resistance to Hydrolysis

This example illustrates the much greater resistance to hydrolysis of the alpha crystalline modification of the compound of formula I as prepared in Example 1 as compared to the lesser resistance of the amorphous form of the compound of formula I as prepared in Example 2.

The test compounds are exposed to 80 % relative humidity at 50° C. and their rate of hydrolysis is monitored by liquid chromatography. The results below are stated in the percent product remaining after 1000 hours of exposure under the conditions stated above.

| Compound of | Percent Product Remaining After 1000 hours |
|---|---|
| Example 1 (alpha crystalline form) | 75 |
| Example 2 (amorphous) | 50 |

EXAMPLE 4

Flowability Properties

This example illustrates the superior flowability properties of the new alpha crystalline modification of the compound of formula I prepared in Example 1 as compared to the flow properties of the compound of formula I as prepared according to the procedure of Example 4 of U.S. Pat. No. 4,318,845.

The angle of repose is measured according to the procedure reported by G. Gold et al. in J. Pharm. Sci., 55, 1291 (1966). A smaller angle of repose indicated a superior flowing solid product.

| Compound of | Angle of Repose (degrees) |
|---|---|
| polypropylene control | 38 |
| Example 1 (alpha crystalline form) | 38 |
| Example 4 of U.S. Pat. No. 4,318,845 (prior art) | 43 |

EXAMPLE 5

Process Stabilization of Propylene at 525° F. (274° C.)

When unstabilized polypropylene containing 0.075% by weight of calcium stearate is admixed with an effective amount of the alpha crystalline form compound of Example 1 and then extruded from an extruder at 525° F. (274° C.), the melt flow rate (in grams/10 minutes) is determined by ASTM method D1238.

The instant alpha crystalline form compound is particularly effective in stabilizing polypropylene against thermal and oxidative degradation as shown by a minimum change in the melt flow rate.

What is claimed is:

1. A process for the preparation of the alpha, monoclinic crystalline form of the compound 2,2′,2″-nitrilo[triethyl-tris-(3,3′,5,5′-tetra-tert-butyl-1,1′-biphenyl-2,2′-diyl) phosphite]which comprises crystallizing or recrystallizing said compound from a mixture of benzene, toluene, o-xylene, m-xylene, p-xylene, 1,2,3-trimethylbenzene, 1,3,5-trimethylbenzene, 1,2,4-trimethylbenzene, 1,2,4,5-tetramethylbenzene, ethylbenzene, cumene, o-cymene, m-cymene, p-cymene, o-diisopropylbenzene or m-diisopropylbenzene and an alkanol of 1 to 3 carbon atoms;

from methyl formate, ethyl formate, methyl acetate, ethyl acetate, n-butyl acetate, isobutyl acetate or amyl acetate;

from diethyl ether, diisopropyl ether or methyl tert-butyl ether; or from a mixture of methylene chloride, chloroform, 1,2-dichloroethane or 1,1,2,2-tetrachloroethane and an alkanol of 1 to 3 carbon atoms.

2. A process according to claim 1 wherein the crystallizing or recrystallizing is from a mixture of benzene, toluene, o-xylene, m-xylene, p-xylene, 1,2,3-trimethylbenzene, 1,3,5-trimethylbenzene, 1,2,4-trimethylbenzene, 1,2,4,5-tetramethylbenzene, ethylbenzene, cumene, o-cymene, m-cymene, p-cymene, o-diisopropylbenzene or m-diisopropylbenzene and an alkanol of 1 to 3 carbon atoms;

3. A process according to claim 2 wherein the crystallizing or recrystalling is from a mixture of toluene and methanol; xylene and methanol; toluene and isopropanol; or, xylene and isopropanol.

4. A process according to claim 1 wherein the crystallizing or recrystallizing is from ethyl acetate or diethyl ether or from a mixture of isopropanol and dichloromethane.

5. A process according to claim 1 wherein the isolated crystalline mass is dried under vacuum at an elevated temperature.

* * * * *